United States Patent [19]

Haining

[11] Patent Number: 5,453,093
[45] Date of Patent: Sep. 26, 1995

[54] DISPOSABLE DENTAL SYRINGE

[76] Inventor: Michael L. Haining, 6731 Ashmore, Houston, Tex. 77069

[21] Appl. No.: 315,704

[22] Filed: Sep. 30, 1994

[51] Int. Cl.$^6$ .................................................. A61M 5/00
[52] U.S. Cl. ........................................... 604/110; 604/218
[58] Field of Search ................................. 604/218, 227, 604/228, 195, 187, 110

[56] References Cited

U.S. PATENT DOCUMENTS

| | | | |
|---|---|---|---|
| 858,025 | 6/1907 | Reese | 604/218 |
| 2,661,740 | 12/1953 | Hickey | 604/228 X |
| 4,687,472 | 8/1987 | Gross | 604/227 |
| 4,888,002 | 12/1989 | Braginetz et al. | 604/218 X |
| 4,950,241 | 8/1990 | Ranford | 604/110 |
| 5,308,329 | 5/1994 | Mazur et al. | 604/110 |
| 5,338,304 | 8/1994 | Adams | 604/195 X |

*Primary Examiner*—J. Yasko
*Attorney, Agent, or Firm*—Richard L. Moseley

[57] ABSTRACT

A disposable retractable needle dental syringe is provided which includes a barrel having a needle carrier mounted therein with a cannula attached thereto. A slidable piston is mounted within the barrel which includes a shaft and hub for locking to the carrier. The plunger seal is conveniently mounted about the shaft between the plunger and the hub. A removable plunger is provided for attachment to and operation of the piston. A cap is provided to cover the open end of the barrel after the carrier and needle have been retracted.

7 Claims, 3 Drawing Sheets

5,453,093

DISPOSABLE DENTAL SYRINGE

BACKGROUND OF THE INVENTION

Due to the recent advent of the AIDS virus, which may be contracted by contaminated hypodermic syringes, there have been several retractable needle hypodermic syringes invented and patented. The retraction of the needle into the barrel of the syringe after use reduces the risk of "needle prick" or the accidental pricking of the person giving the injection after the syringe has been used.

Some of the recently patented retractable needle syringes include U.S. Pat. Nos. 4,692,156 (Hailer); 4,675,005 (DeLuccia); 4,747,830 (Gloyer, et al); and my own Pat. Nos. 4,790,822 and 4,950,251. All of the syringes disclosed include a hypodermic needle mounted on a carrier which is slidable in the barrel. The plunger is locked to this carrier after the injection has been given and is withdrawn up into the barrel by withdrawal of the plunger. The simplest mechanism for locking the plunger to the carrier is disclosed as a projection on the lower end of the plunger which engages through an opening in the upper end of the carrier. Thus, the engagement requires a simple extra push on the plunger. There is the possibility that the plunger might become accidently engaged before use rendering the syringe useless. The present inventor has thus seen a need for a simple device to prevent depression of the plunger prior to use.

Dental syringes are used to administer local anesthetic and generally include a stainless steel barrel which accepts a glass vial of the anesthetic such as novocaine.

SUMMARY OF THE INVENTION

The present invention comprises a disposable dental syringe designed to be shipped with a pre-loaded quantity of anesthetic. The syringe comprises a hollow cylindrical barrel open at both ends with finger flanges at the upper end and an inwardly projecting lip at the lower end. A rigid needle carrier of hard plastic is seated within the barrel on the lip with a projection extending out of the barrel for attachment of a standard hypodermic needle or cannula (the words are used interchangeably herein). A piston having a rubber seal at the lower end is located within the barrel at the upper end and adjacent the fluid contained therein. A separate plunger is provided which is adapted to lock onto the piston for operation. The plunger is provided separately for shipping purposes. A shaft extends from the lower end of the piston which terminates in a hub. The hub is adapted to fit and lock into an enlarged bore near the upper end of the carrier. The piston seal conveniently fits around the shaft between the end of the plunger and the hub. The hub clicks and locks into the carrier after use, allowing the carrier and needle to be retracted into the barrel.

DETAILED DESCRIPTION OF THE PREFERRED EMBODIMENT

For a detailed description of the preferred embodiment the reader is directed to the accompanying figures in which like components are given like numerals for ease of reference.

Figure 1:
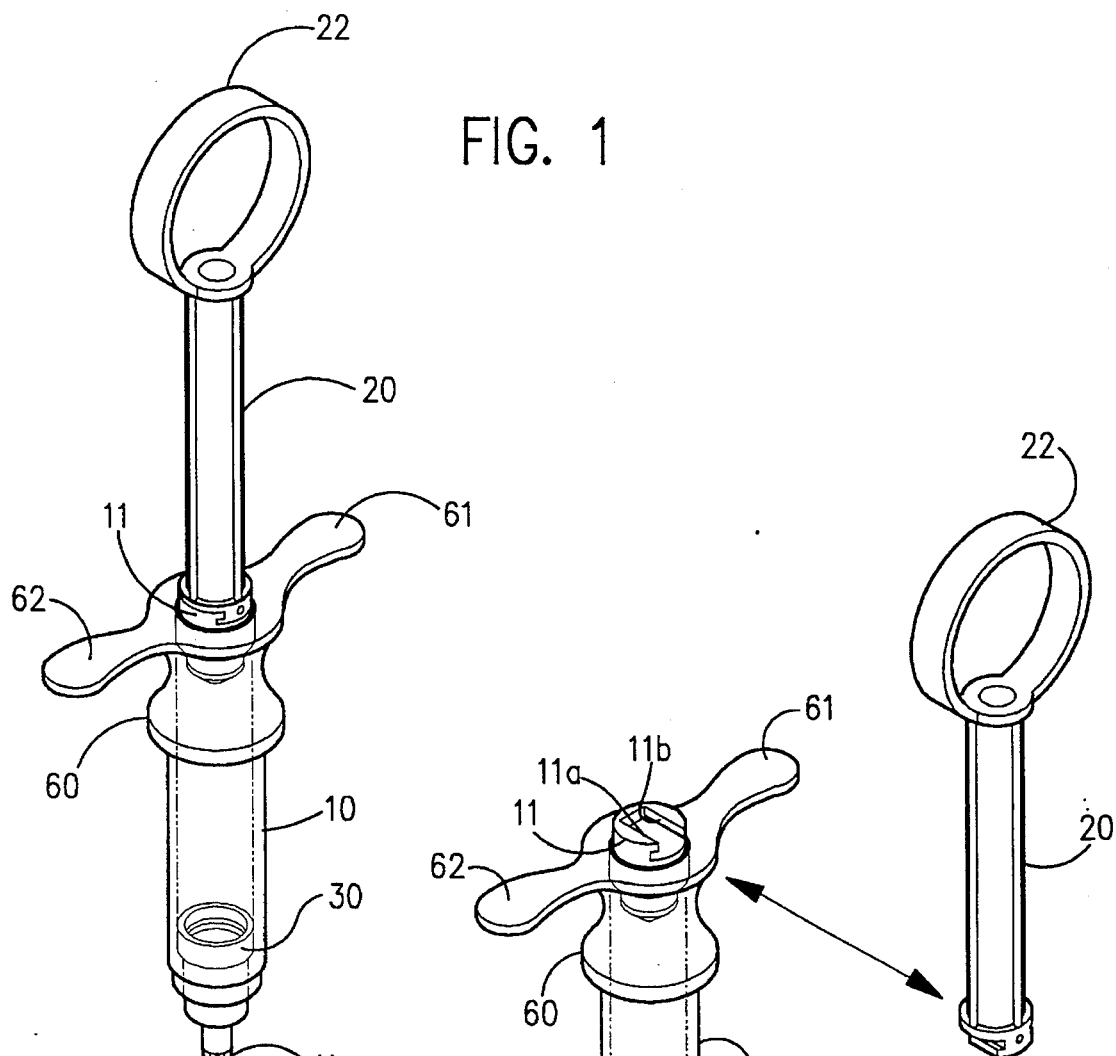
FIG. 1 is a perspective view of the retractable needle dental syringe of the present invention.
Figure 2:
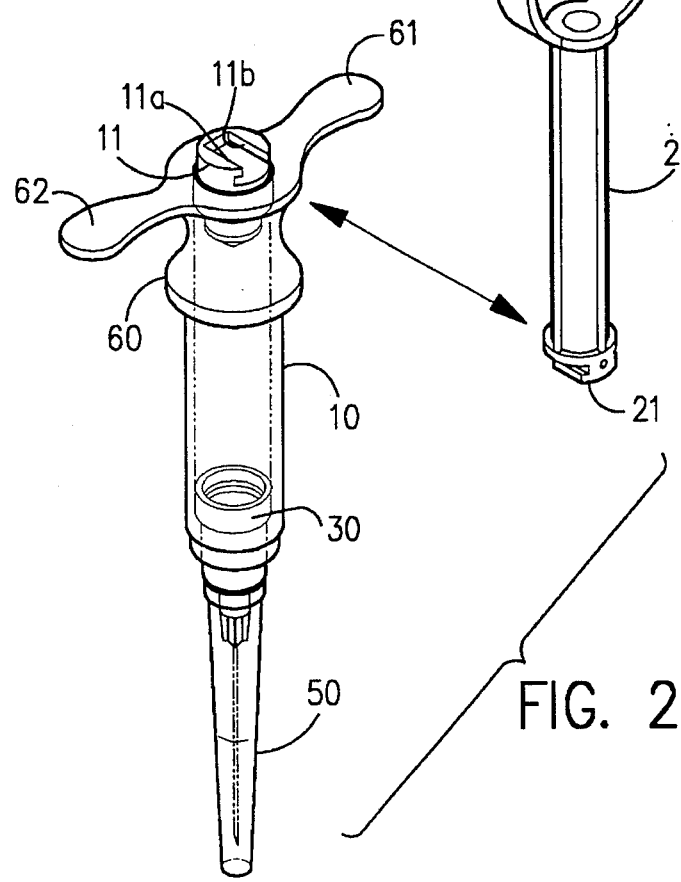
FIG. 2 is a perspective view of the retractable needle dental syringe of the present invention showing the plunger and piston separated.

Referring first to FIGS. 1 and 2 the dental syringe is shown to comprise a hollow cylindrical barrel 10 having finger flanges 61 and 62 at the upper end and a needle carrier 30 at the lower end. Cannula 40 and 41 is mounted on the needle carrier 30 such that the cannula extend from the barrel 10. Piston 11 is located at the upper end of the barrel 10 when the syringe is filled with solution and shipped. As discussed below plunger 20 may be attached to the piston 11. The plunger 20 includes a ring 22 at the upper end for receiving the thumb of the user to manipulate the entire syringe.

Figures 3, 4:
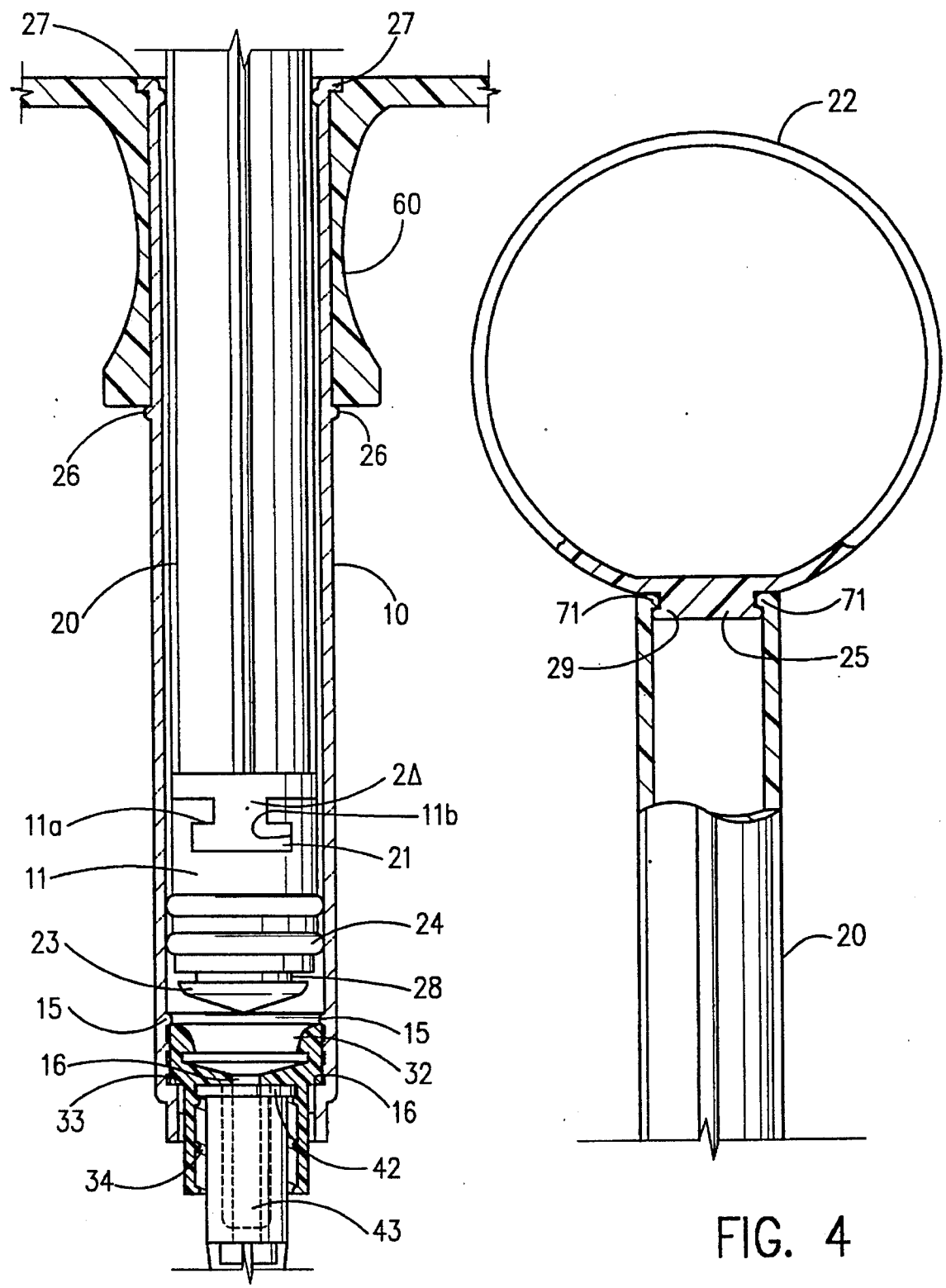
FIG. 3 is a side elevational view in partial cross section showing the detail of the needle carrier and hub.
FIG. 4 is a side elevational view in partial cross section showing the detail of the upper end of the plunger.

Referring now to FIGS. 3 and the details of the needle carrier 30, hub 23 and finger flanges 61 and 62 are shown. The finger flanges are part of a separate piece 60 which is rotatably secured about the barrel 10 by external ridge 26 at the lower end and by flange 27 at the upper end. The finger flange piece 60 is thus freely rotatable about the barrel.

The cylindrical hollow barrel 10 is made of semi-rigid deformable plastic. A rigid needle carrier 30 of hard plastic is inserted into the barrel 10 through the upper end opening and is seated on a lip 16 such that the extension 31 protrudes out of the barrel 10. A cannula 40 and is attached to extension 31 by leuer lock 42 which engages internal threads 34 in extension 31. The cannula is provided with protective sheath 50 (FIG. 2) for protection before use.

The outer diameter of the carrier is sized to provide a snug friction seal with the inner walls of the barrel 10. An internal ridge 15 within barrel 10 is located directly above the carrier 30 to aid in retaining the carrier in position while giving an injection. As noted, the leuer lock 41 of cannula 40 is secured to extension 31 by the engagement of flange 42 with internal threads 34. A central bore 33 extends through the carrier 30 to provide fluid communication between the cannula passage 43 and barrel 10. Near the upper end of central bore 33 is an enlarged bore 32.

Piston 11 is slidably mounted within barrel 10. Shaft 28 extends from the lower end of the piston 1. At the lower end of shaft 28 is a hub 23 which is adapted to fit and lock into enlarged bore 32 in carrier 30. A rubber seal 24 is conveniently fit about shaft 28 for sealing engagement with the internal wall of barrel 10. The plunger 20 is attached to the piston 11 by a T type connection wherein the head 21 of the T is slid into channels 11a and 11b formed into the top of the piston 11.

Referring now to FIG. 4 there is shown a detail of the upper end of the plunger. The plunger body 20 is shown to be a hollow cylinder with an inward projecting lip 71 about the upper end. Ring 22 includes a projection 25 which extends into the hollow body 20. The ring 22 is rotatably held in place by the action of outward projections 29 acting against inward projecting lip 71. The ring and finger flanges are thus independently rotatable about the longitudinal axis of the syringe body 10.

Figure 5:
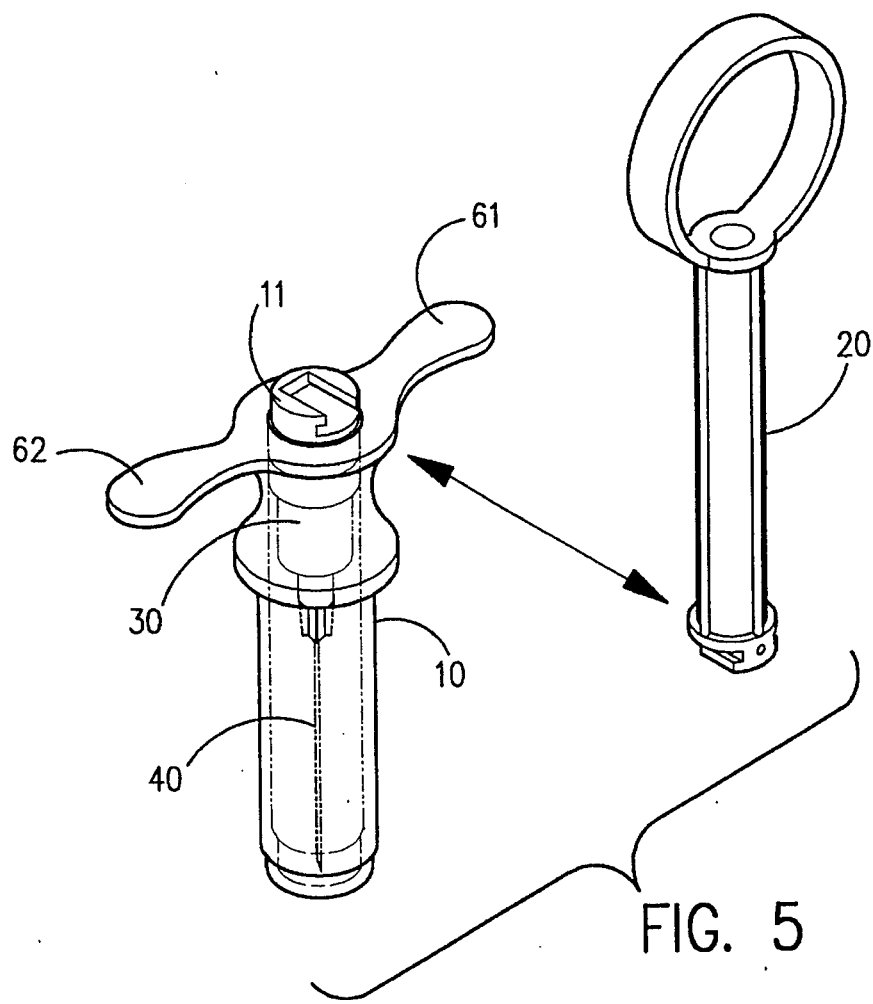
FIG. 5 is a perspective view of the syringe after use with the cannula retracted.
Figure 6:
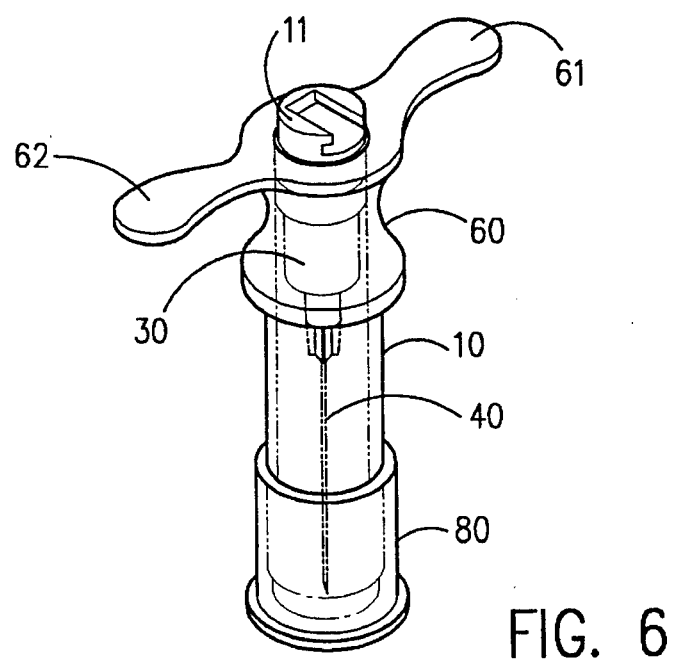
FIG. 6 is a perspective view of the syringe after use with the cannula retracted and a the end capped.

Referring now to FIGS. 5 and 6 the used syringe is shown.

The carrier 30 with cannula 40 is withdrawn into barrel 10 and the plunger 20 is removed. A cap 80 is placed over the now open lower end of the syringe to make a complete sealed unit.

It is anticipated that each syringe will be shipped pre-filled with a specific amount of solution of desired strength. The loaded syringe may used as a standard dental syringe with the freely rotating finger flanges and ring allowing for proper maneuverability during administration of the solution. As soon as the cannula is withdrawn from the recipient, the user may then further depress the plunger 20 and piston 11 until the hub 23 engages the carrier 30. After the hub 23 has engaged the carrier 30 the needle carrier with cannula 40 may then be retracted into the barrel 10. The plunger 20 may be disconnected from the piston 11 to make a more compact unit and the cap 80 placed over the open end.

All of the materials of construction are conventional. For example, the barrel may be of transparent hard or soft plastic as is now commonly used in disposable syringes. The plunger and needle carrier are of hard plastic with the plunger seal and O ring being of standard rubber suitable for medical purposes.

What is claimed is:

1. A disposable single use piston syringe comprising:

a hollow cylindrical barrel open at both ends and having an inwardly projecting lip at the lower end and finger flanges at the upper end;

a rigid cylindrical needle carrier mounted within said barrel and seated on said lip and retained in place by frictional sealing engagement between the outer diameter of said needle carrier and the inner wall of said barrel, said needle carrier having an extension protruding through the opening at the lower end of said barrel;

a hypodermic needle mounted on said extension;

a piston slidably mounted in said barrel through the upper open end and defining a fluid chamber between said carrier and said piston, said piston having channels at the upper end;

a plunger for attachment to said piston and extending out said upper end, said plunger having a T type connector for engagement with said channels and attachment to said piston;

a central bore through said carrier and extension for fluid communication between said needle and said chamber;

an enlarged bore in said carrier near said chamber and coaxial with said central bore;

a shaft extending from the lower end of said plunger; and a hub on the lower end of said shaft adapted to lock into said enlarged bore.

2. The piston syringe of claim 1 wherein said finger flanges are rotatably secured about said barrel.

3. The piston syringe of claim 1 wherein said plunger further comprises a ring at the upper end.

4. The piston syringe according to claim 1 further comprising a plunger seal member secured about said shaft between said plunger and said hub.

5. The piston syringe of claim 1 further comprising an internal ridge within said barrel directly above said needle carrier.

6. The piston syringe of claim 3 wherein said ring is freely rotatable about the end of said plunger.

7. A disposable single use piston syringe comprising:

a hollow cylindrical barrel open at both ends and having an inwardly projecting lip at the lower end;

finger flanges rotatably mounted about said barrel at the upper end;

a rigid cylindrical needle carrier mounted within said barrel and seated on said lip and retained in place by frictional sealing engagement between the outer diameter of said needle carrier and the inner wall of said barrel, said needle carrier having an extension protruding through the opening at the lower end of said barrel;

an internal ridge within said barrel directly above said needle carrier a hypodermic needle mounted on said extension;

a piston slidably mounted in said barrel through the upper open end and defining a fluid chamber between said carrier and said piston, said piston having channels at the upper end;

a plunger for attachment to said piston and extending out said upper end, said plunger having a T type connector for engagement with said channels and attachment to said piston;

a ring rotatably mounted on the upper end of said plunger;

a central bore through said carrier and extension for fluid communication between said needle and said chamber;

an enlarged bore in said carrier near said chamber and coaxial with said central bore;

a shaft extending from the lower end of said plunger;

a hub on the lower end of said shaft adapted to lock into said enlarged bore; and a plunger seal member secured about said shaft between said plunger and said hub.

* * * * *